United States Patent [19]
Kowalski et al.

[11] Patent Number: 5,137,175
[45] Date of Patent: Aug. 11, 1992

[54] FLUID STORING AND DISPENSING

[75] Inventors: Henry C. Kowalski, Grand Blanc; Brenton L. Friday, Flint, both of Mich.

[73] Assignee: GMI Engineering & Management Institute, Flint, Mich.

[21] Appl. No.: 486,591

[22] Filed: Feb. 28, 1990

[51] Int. Cl.⁵ .............................. G01F 11/00
[52] U.S. Cl. ............................ 222/1; 222/95; 222/105; 222/386.5; 222/528; 141/24; 141/83; 141/114
[58] Field of Search .......... 222/1, 56, 77, 207, 222/211, 212, 215, 95, 105, 386.5, 183, 131, 182, 541, 538, 527; 141/21, 24, 26, 25, 83, 114; 220/31, 85 B, 903, 904; 604/132; 251/4

[56] References Cited
U.S. PATENT DOCUMENTS

| | | | |
|---|---|---|---|
| 1,392,861 | 10/1921 | Tabacco | 446/217 |
| 2,011,884 | 8/1935 | Watkins | 222/131 |
| 3,025,634 | 3/1962 | Barricks | 446/187 |
| 3,349,965 | 10/1967 | Krugger | 222/183 |
| 3,486,539 | 12/1969 | Jacuzzi | 141/329 |
| 3,656,478 | 4/1972 | Swersey | 222/56 |
| 3,672,543 | 6/1972 | Roper et al. | 222/212 |
| 3,684,124 | 8/1972 | Song | 222/541 |
| 3,738,538 | 6/1978 | Roper et al. | 222/183 |
| 3,791,557 | 2/1974 | Venus, Jr. | 222/105 |
| 3,876,115 | 4/1975 | Venus, Jr. et al. | 222/183 |
| 3,940,026 | 2/1976 | Kain | 222/212 |
| 3,993,069 | 11/1976 | Buckels et al. | 222/386.5 |
| 4,121,737 | 10/1978 | Kain | 222/95 |
| 4,134,228 | 1/1979 | Ortiz | 46/88 |
| 4,222,499 | 9/1980 | Lee et al. | 222/183 |
| 4,257,460 | 3/1981 | Paranay et al. | 141/26 |
| 4,324,350 | 4/1982 | Thompson | 222/212 |
| 4,386,929 | 6/1983 | Peery et al. | 222/212 |
| 4,387,833 | 6/1983 | Venus, Jr. | 222/95 |
| 4,419,096 | 12/1983 | Leeper et al. | 604/132 |
| 4,423,829 | 1/1984 | Katz | 222/95 |
| 4,458,830 | 7/1984 | Werding | 222/131 |
| 4,555,295 | 11/1985 | Orikasa et al. | 156/349 |
| 4,658,990 | 4/1987 | Ranage | 222/212 |
| 4,735,239 | 4/1988 | Salmon et al. | 141/25 |
| 4,915,693 | 4/1990 | Hessel | 604/132 |

FOREIGN PATENT DOCUMENTS 8603978 7/1986 European Pat. Off. ............ 604/132

Primary Examiner—Donald T. Hajec
Assistant Examiner—Philippe Derakshani
Attorney, Agent, or Firm—Brooks & Kushman

[57] ABSTRACT

A fluid storing and dispensing apparatus (10) is disclosed as having a tubular rubber bladder (12) to store a fluid, a valve (24) to regulate fluid flow from the bladder, and a support (26) that maintains the bladder in a longitudinally stretched condition to initiate desired inherent properties that provide a substantially constant fluid discharge pressure and a greater number of fill cycles prior to bladder failure than is obtainable with an unstretched bladder. Another embodiment includes a container (28) to surround and restrict the maximum diameter of the bladder to limit lateral deformation and thereby considerably increase the number of fill cycles prior to bladder failure. A system (50) for replenishing the fluid storing and dispensing apparatus is also disclosed.

30 Claims, 10 Drawing Sheets

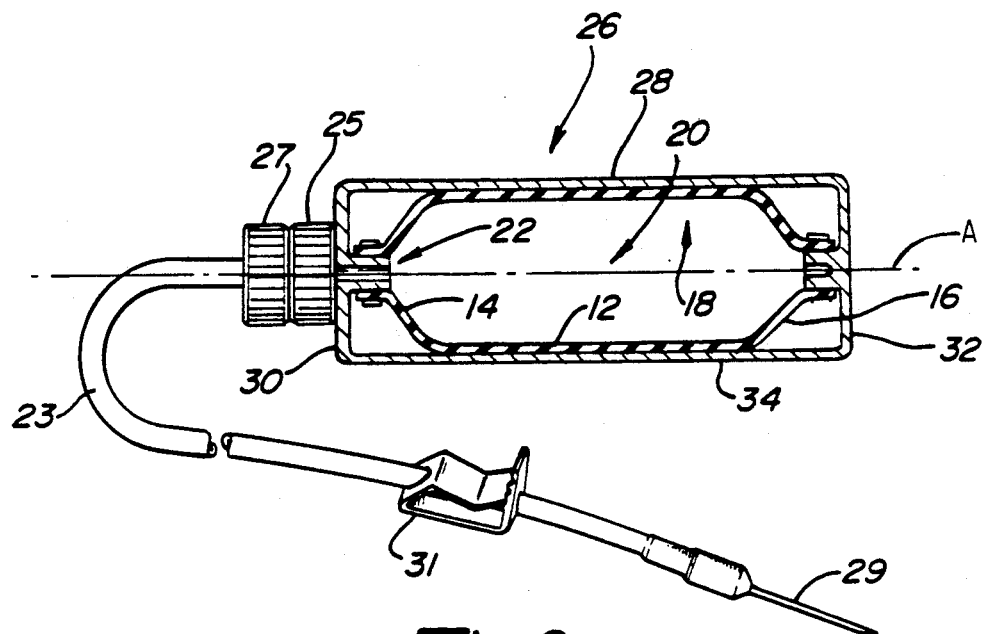
_Fig-9_
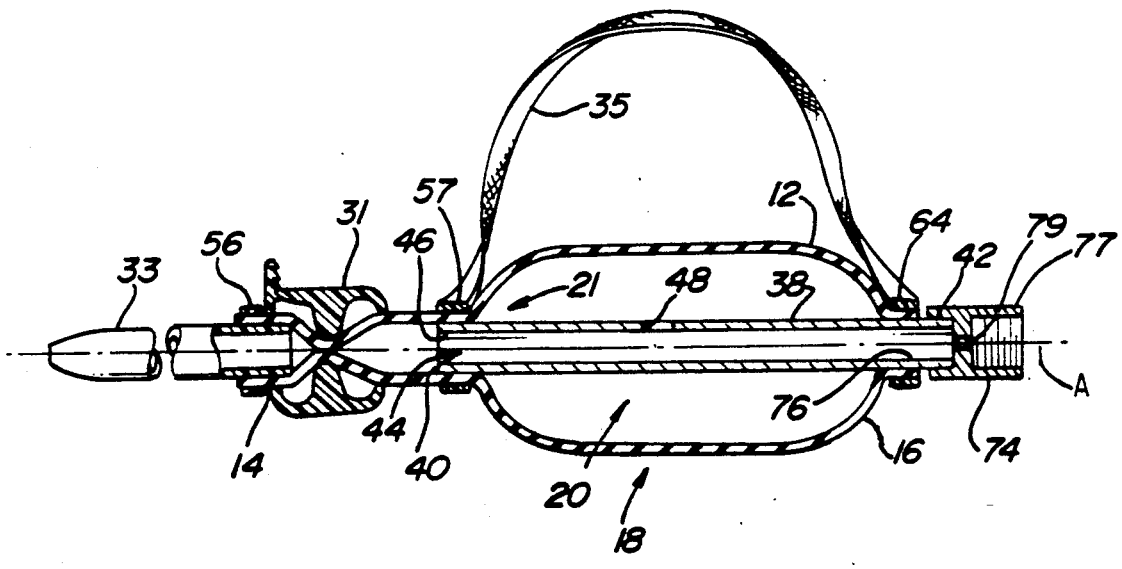
_Fig-10_

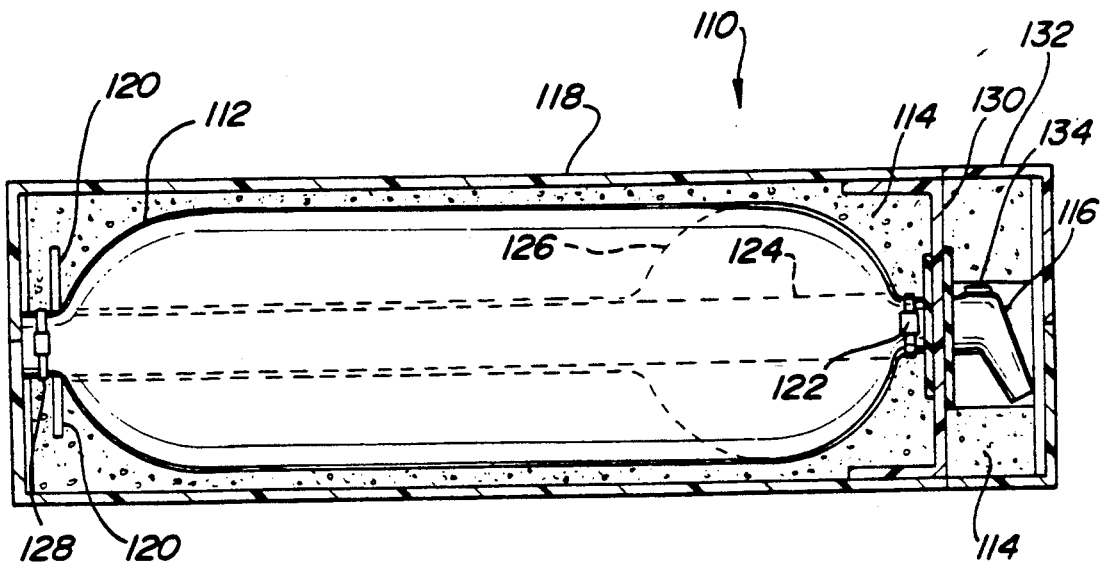
Fig-13
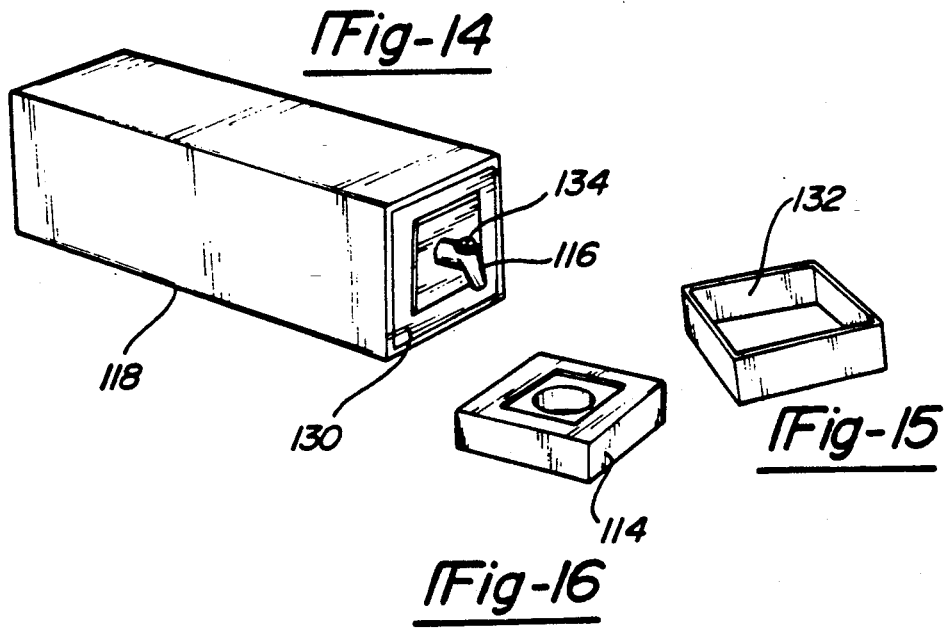
Fig-14
Fig-15
Fig-16

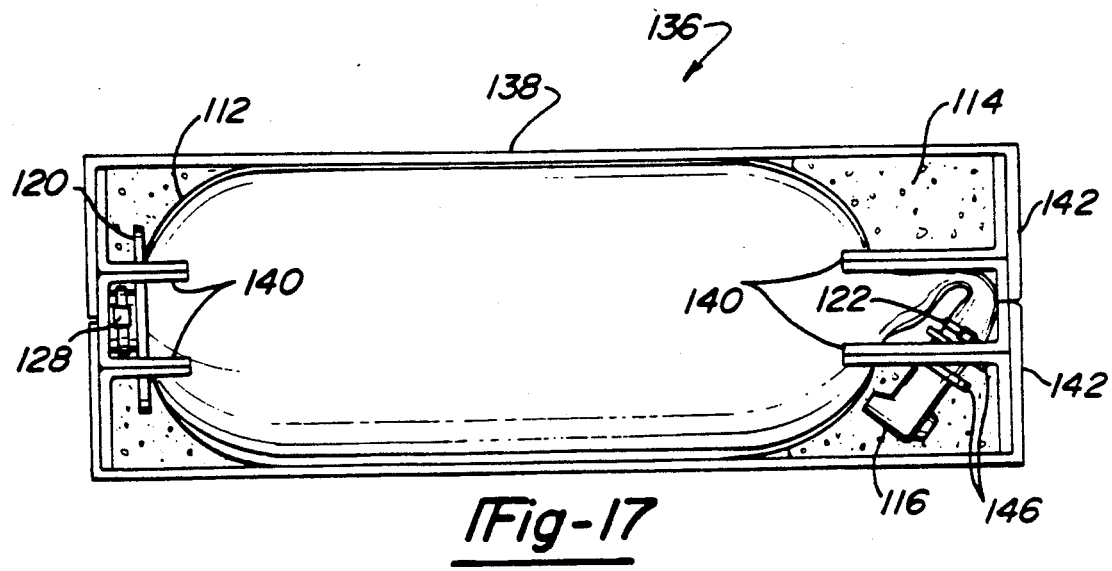
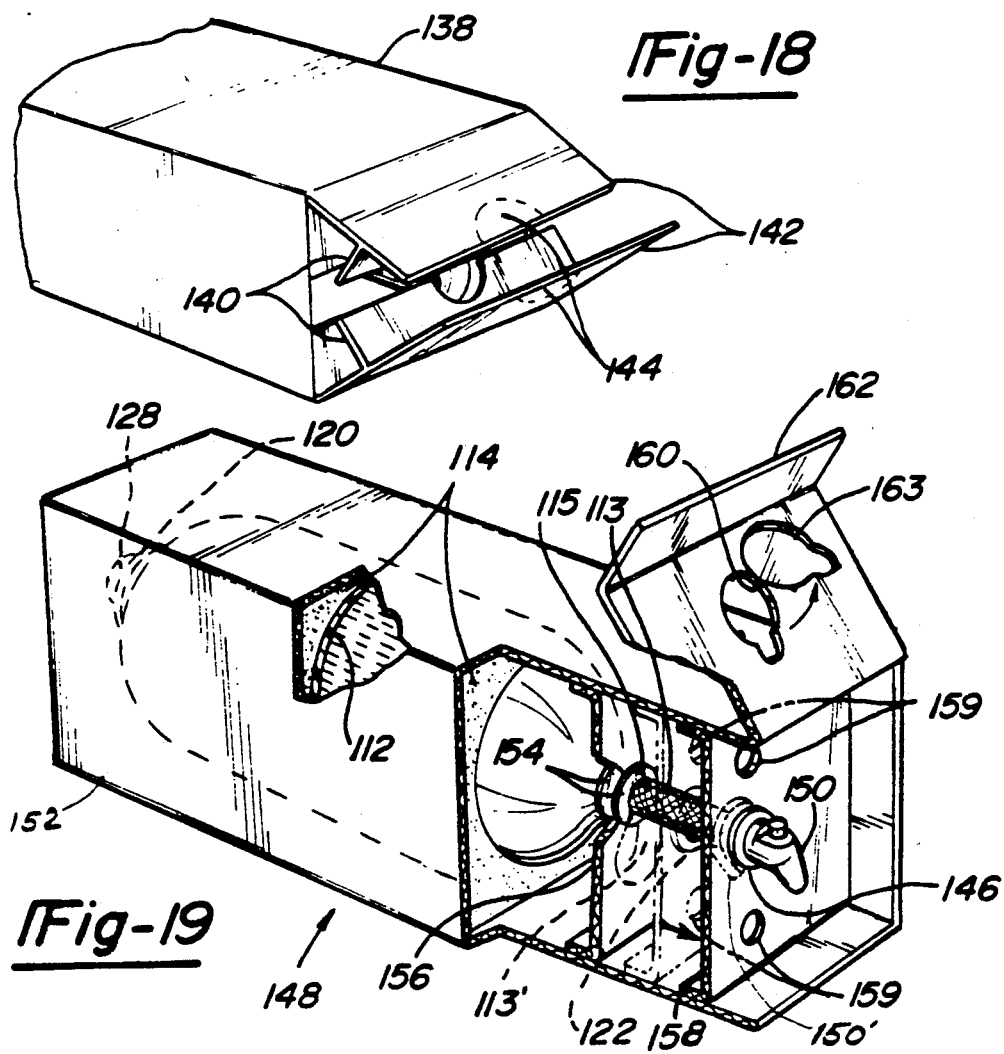

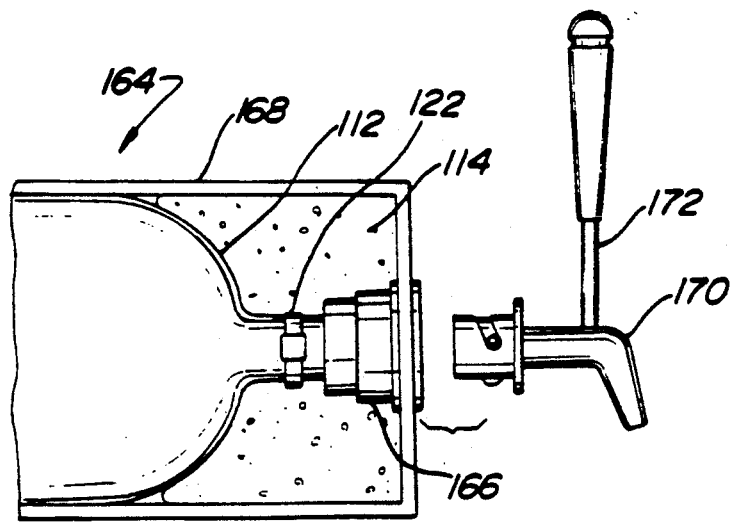
Fig-20a
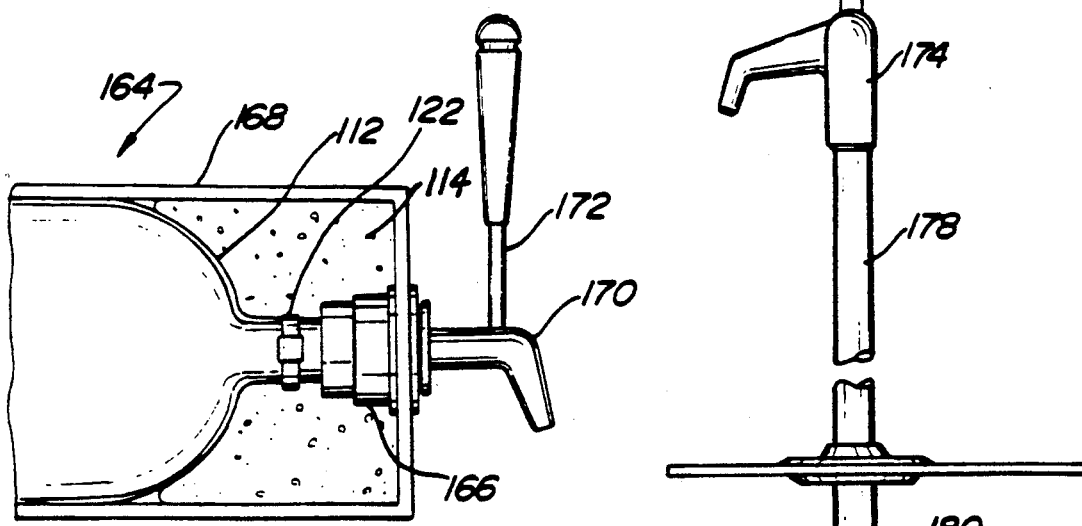
Fig-20b
Fig-21
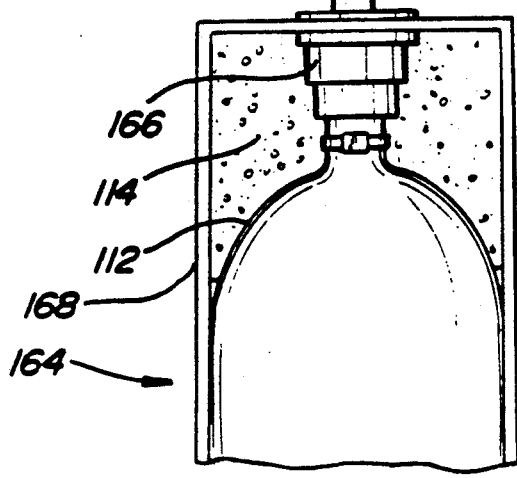

FLUID STORING AND DISPENSING

TECHNICAL FIELD

This invention relates to fluid storing and dispensing devices using elastic bladders to dispense fluids at substantially constant pressures.

BACKGROUND ART

This invention is related to the Liquid Projecting Device disclosed in U.S. Pat. No. 4,735,239, by Michael E. Salmon and John S. Briski, which is incorporated by reference. The referenced device employs a tubular elastic bladder for receiving a liquid, a nozzle affixed to the bladder for projecting a stream of liquid, and a control valve for regulating the discharge.

The referenced device is perfectly adequate for its intended purpose of projecting a liquid and represents significant advances over prior art, but it was not designed for the purpose of storing and dispensing fluids at substantially constant pressures and of storing fluids in a substantially chemically inert and impermeable environment for long periods.

Other fluid storing and dispensing devices using elastic bladders have been known for some time. Refer, for example, to the flowable substances dispenser disclosed by U.S. Pat. No. 3,672,543 to Roper et al. This dispenser includes an expandable bladder and a unitary mandrel and valve closure member supported by a container. The bladder is made of an elastomeric material, such as natural latex or silicone rubber, and appears to be formed by a dipping process rather than by extrusion. It has an opening at one end and extends therefrom in portions having various inside diameters. The mandrel fits inside the bladder, maintaining it in a longitudinally stretched condition which serves to provide force to dispell fluids disposed therewithin when the valve is opened.

U.S. Pat. No. 3,738,538 to Roper et al. also discloses a dispenser for flowable substances. This dispenser includes a similar bladder, but it is held in a longitudinally stretched condition by disposing a spherical member inside its closed end and retaining the member with a snap fitting mounted on the container. The bladder is twisted to force out through the valve all fluid contained within the bladder.

U.S. Pat. No. 3,791,557 to Venus discloses a nonaerosol container having an expandable bladder and a sheath for providing expelling force. The device includes an expandable bladder, a mandrel, a sheath and a valve closure member supported by a container. The bladder is made of an elastomeric material, such as natural latex or silicone rubber that is chemically compatible with whatever fluid is to be stored within it, and appears to be formed by a dipping process rather than by extrusion. It has an opening at one end and extends therefrom, having an ever decreasing inside diameter, to a closed end. The mandrel fits inside the bladder without expanding it. The bladder, in turn, fits within a sheath. The sheath is a tube, open at each end, made of latex or natural rubber having a high modulus of elasticity, the sheath furnishing most of the fluid expelling force.

A double expansible bladder container is disclosed by Venus in U.S. Pat. No. 3,876,115. The device includes a pair of bladders. A first bladder, made of a butyl-like elastomer, is designed to be chemically compatible with whatever fluid is to be stored within it. A second bladder, made of a latex-type compound, is designed to substantially surround the first and is the primary source of the fluid expelling force. The mandrel used in this device is only slightly longer than the first bladder.

A liquid dispensing and metering assembly is disclosed in U.S. Pat. No. 3,486,539 by Jacuzzi. The disclosed assembly includes an expansible receptacle of a material adapted to maintain constant pressure characteristics over a substantial change in volume of liquid content of the receptacle. The assembly discharges through a slow-rate metering element to provide a uniform discharge flow at a low, constant pressure.

U.S. Pat. No. 4,419,096 to Leeper et al. discloses an elastomeric bladder assembly designed to operate at a constant pressure to maintain a constant dispensing rate. The assembly includes a bladder having within its lumen a bolus forming means that prevents the bladder from collapsing to a cylindrical configuration, thereby inhibiting a sharp rise in pressure just prior to the end of a duty cycle.

U.S. Pat. No. 4,432,829 to Katz discloses an apparatus for containing and dispensing fluids under pressure. The apparatus includes a flexible, chemically inert container having longitudinally extending creases to provide for radially inward folding of the container when being emptied and radially outward expansion when being filled. An open-ended, radially elastic, tubular, fabric sleeve surrounds the container when folded. An open-ended, tubular, resilient member is disposed about the fabric sleeve when the container is folded. The resilient member is controlled by frictional interaction with the fabric sleeve, which enables the resilient member to expand in substantially radial directions when the container is filled with a fluid under pressure.

While each of these devices functions with a certain degree of efficiency, none disclose the means of the present invention for providing the advantage of substantially eliminating the rises in pressure that occur proximate the bladder fill times as well as those that occur proximate the discharge times; and none disclose the means of the present invention for providing the advantage of considerably increasing the number of fill cycles prior to bladder failure.

Other fluid storing and dispensing devices using elastic bladders are disclosed by U.S. Pat. Nos. 1,392,861; 3,025,634; 3,940,026; 4,121,737; 4,134,228; 4,222,499; 4,257,460; 4,324,350; 4,387,833; 4,555,295; and 4,458,830.

DISCLOSURE OF THE INVENTION

An object of the present invention is to provide an apparatus having a fluid storing bladder that fills, stores and dispenses fluids at a substantially constant pressure with respect to the displacement of the bladder.

Another object of the present invention is to provide an apparatus capable of functioning effectively during a considerably large number of fill cycles prior to bladder failure.

Yet another object of the present invention is to provide an apparatus that uses a bladder that is chemically inert and impermeable with respect to the fluid contained and also with respect to ambient elements such as oxygen.

Still another object of the present invention is to provide an apparatus that will dispense substantially all the fluid stored therein.

Another object of the invention is to provide an apparatus that can be fabricated easily, inexpensively and in sizes convenient for specific applications such as storing and dispensing water, carbonated beverages, insecticides, intravenous solutions, and the like.

In carrying out the foregoing and other objects, the fluid storing and dispensing apparatus of the present invention includes a tubular rubber bladder internally defining in a central region thereof a fluid storage cavity, a valve to regulate the flow of fluid to and from the fluid storage cavity, and a support connected to the bladder.

In a preferred embodiment disclosed, the support maintains the bladder initially longitudinally stretched sufficiently to provide a substantially constant fluid pressure with respect to the displacement of the fluid storage cavity. The fluid storing and dispensing apparatus of the present invention includes a tubular rubber bladder having first and second ends and a central region therebetween disposed along a longitudinal axis. The central region internally defines a fluid storage cavity, and at least one of the ends of the bladder forms an orifice therein to admit and/or discharge fluid. A valve is connected to the orifice to regulate the flow of fluid to and from the fluid storage cavity.

A support is connected to the bladder to maintain it initially longitudinally stretched sufficiently to provide a substantially constant fluid pressure with respect to the displacement of the fluid storage cavity. Stretching the bladder also significantly increases the number of fill cycles prior to bladder failure. The support includes a cylinder having a first end connected to the first end of the bladder and a second end connected to the second end of the bladder.

The cylinder forms a container that surrounds the bladder and has a diameter less than the maximum diameter and expansion limit of the bladder. The container serves to limit the radial expansion of the bladder, and its use substantially increases the number of fill cycles prior to bladder failure.

A sensing switch may be mounted to the container to position it proximate the bladder. The sensing switch may typically be a bistable device that is transferred to a first state when the bladder is inflated beyond a minimum amount and transferred to a second state when the bladder is deflated below that minimum amount. The sensing switch may be readily incorporated into an electrical circuit designed, for example, to maintain the fluid stored in the bladder between desired limits.

In an alternative embodiment, a rod extends along the longitudinal axis of the bladder, and a first end of the rod extends through the bladder orifice. A second end of the rod is connected to the second end of the bladder. The outside diameter of the rod is at least equal to the initial inside diameter of the longitudinally stretched but uninflated bladder. The rod has a generally longitudinal lumen having an opening proximate the first rod end extending through the bladder orifice and at least a second opening proximate the midportion of the fluid storage cavity.

In various embodiments, the rod may serve as an internal bladder support to maintain the bladder in an initially longitudinally stretched condition. It may also serve to facilitate filling and emptying the bladder by virtue of its lumen, which provides a fluid path between the first end of the rod extending through the bladder orifice and the fluid storage cavity defined inside the bladder. By virtue of the fact that the outside diameter of the rod is at least as great as the inside diameter of the longitudinally stretched but uninflated bladder, the rod may also serve as a fluid dissipating core to facilitate completely emptying the bladder by ensuring that there is no fluid storage space between the outside surface of the rod and the inside surface of the deflated bladder when the latter is deflated.

An additional embodiment disclosed provides a replenishing fluid storing and dispensing system including the elements in the combination just described and additionally having a pump connected between a source of fluid, which might be a reservoir or the like, and the bladder. The pump is responsive to the state of the sensing switch and transfers fluid from the source to the bladder fluid storage cavity whenever the amount of fluid remaining in the bladder is reduced below a desired minimum.

Another embodiment of the present invention includes an elongated, elastic bladder, insulating material, a valve mechanism, and a housing. The insulating material is disposed within the housing, and the bladder is substantially encased within the insulating material. The valve mechanism is secured to one end of the elongated bladder.

The insulating material has an outer configuration conforming to the inside shape of the housing and an inner configuration conforming to the outer shape of the expanded bladder. The housing and the insulating material thus cooperate to support the bladder when the latter is expanded. The overall dimensions of the housing may be conveniently chosen for specific applications such as storing carbonated beverages in a home refrigerator.

The housing may have a movable or removable portion, for example, a perforated section of housing material, a tear-away paper band, removable tape, a folding flap, or the like, to provide access to the valve mechanism. With the portion in place, the valve mechanism is protectively confined and isolated from contaminants and physical abuse. With the portion removed, the valve mechanism is accessible for easy operation. A handle or handles may be attached to the housing to make it convenient to carry.

The valve mechanism has a body that defines a channel for conducting an exiting flow away from the bladder and that connects the valve mechanism to the bladder. The valve mechanism also has a valve seat formed, and a valve member effectively disposed, therewithin. A valve operating member is mounted in the body of the valve mechanism for positioning the valve member with respect to the associated valve seat, the valve mechanism normally inhibiting an exiting flow of the fluid stored within the bladder when the valve member is positioned against the valve seat and allowing an exiting flow when the valve member is positioned away from the valve seat, the rate of flow being a function of the distance between the valve member and the valve seat.

The bladder may be made from commonly available rubber tubing such as that made from latex. Such material is relatively chemically inert and impermeable with respect to fluids that might commonly be stored in the bladder and also with respect to ambient elements such as oxygen.

Since the bladder may be made from a commonly available material and the other elements of the fluid storing and dispensing apparatus may also be easily made or obtained from readily available sources, the apparatus can be fabricated easily, inexpensively and in forms tailored for specific applications.

The objects, features and advantages of the present invention are readily apparent from the following detailed description of the best mode for carrying out the invention when taken in connection with the accompanying drawings.

BRIEF DESCRIPTION OF THE DRAWINGS

In the drawings, in which like reference characters indicate corresponding parts in all the views:

FIG. 9 is a view, partly in section, of another embodiment of the invention as it might be used in another application;

FIG. 10 is a sectional view of yet another embodiment of the invention;

FIG. 13 is a side view, partly in section, of the preferred embodiment of the invention and shows the device in empty, partially filled and fully filled states;

FIGS. 14, 15 and 16 are perspective views of the device of FIG. 13 shown partially disassembled;

FIG. 17 is a side view, partly in section, of another embodiment of the invention;

FIG. 18 is a perspective view of the device of FIG. 17 shown partially opened;

FIG. 19 is a side view, partly in section, of yet another embodiment of the invention;

FIG. 20 is a partial side view FIGS 20a and 20b are partial side views, partly in section, of another embodiment of the invention and respectively show an element thereof in an unconnected and in a connected position;

FIG. 21 is a partial side view, partly in section, of still another embodiment of the invention.

BEST MODES FOR CARRYING OUT THE INVENTION

Figure 1:
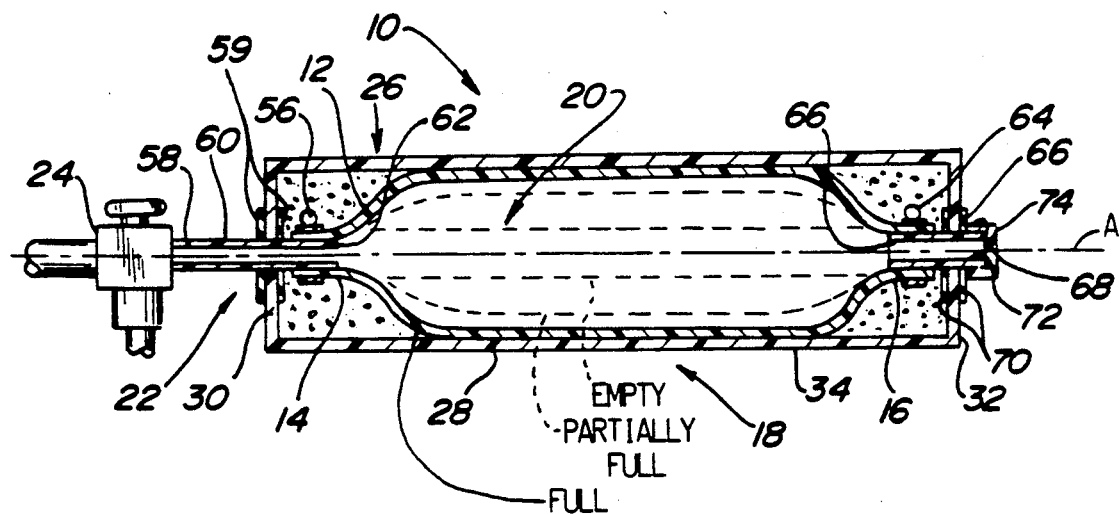
FIG. 1 is a side view, partly in section, of the preferred embodiment of the invention and shows the apparatus in empty, partly filled and full states.

With reference to FIG. 1 of the drawings, a fluid storing and dispensing apparatus constructed in accordance with the present invention is generally indicated by the reference character 10. The device includes a tubular rubber bladder 12 having a first end 14 and a second end 16 and a central region generally indicated by the reference character 18 therebetween disposed along a longitudinal axis A. The central region 18 internally defines a fluid storage cavity generally indicated by the reference character 20, and at least one of the ends of the bladder 12 forms an orifice generally indicated by the reference character 22 therein to admit and/or discharge fluid. A valve 24 is connected to the orifice 22 to regulate the flow of fluid to and from the fluid storage cavity 20.

A support generally indicated by the reference character 26 is connected to the bladder 12 to maintain it initially longitudinally stretched sufficiently to provide a substantially constant fluid pressure with respect to the displacement of the fluid storage cavity 20. Stretching the bladder 12 sufficiently also significantly increases the number of fill cycles prior to bladder failure. The support 26 includes a cylinder 28 having a first end 30 connected to the first end 14 of the bladder 12 and a second end 32 connected to the second end 16 of the bladder.

The connection of the first end 30 of the cylinder 28 to the first end 14 of the bladder 12 is accomplished by connecting, with a first clamp 56, the first end 14 of the bladder 12 to a first end 58 of a first bladder connection tube 60, which extends through the first end 30 of the cylinder 28 and is secured in position by first locknuts 59. A second end 62 of the first bladder connection tube 60 is connected to the valve 24. The connection of the second end 32 of the cylinder 28 to the second end 16 of the bladder 12 is accomplished by connecting, with a second clamp 64, the second end 16 of the bladder 12 to a first end 66 of a second bladder connection tube 68, which extends through the second end 32 of the cylinder 28 and is secured in position by second locknuts 70. A second end 72 of the second bladder connection tube 68 is closed by a cap 74 or may be connected to a bladder filling device (not shown).

The cylinder 28 forms a container 34 that surrounds the bladder 12 and has a diameter less than the maximum diameter and expansion limit of the bladder 12. The container 34 serves to limit the radial expansion of the bladder 12, and its use substantially increases the number of fill cycles prior to bladder failure.

Figure 2:
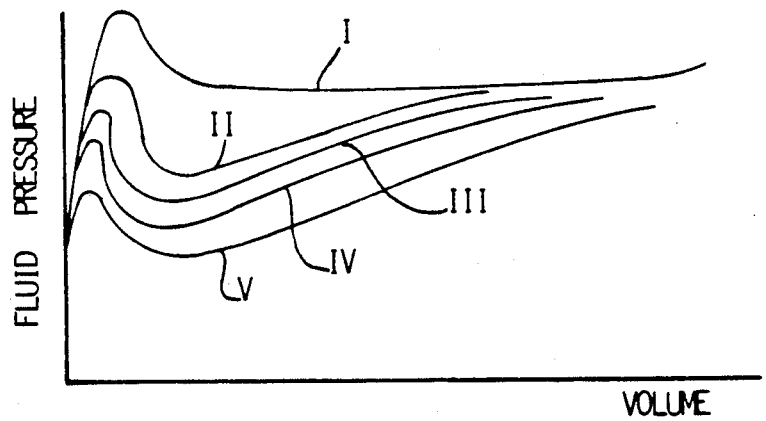
FIG. 2 is a graphic representation of fluid pressure characteristics with respect to storage cavity displacement for a bladder unstretched and stretched longitudinally by amounts ranging approximately from 25 to 150 percent.

In the preferred embodiment of the present invention, the bladder 12 is formed of a tube made of a material such as polyisoprene having a cis-polyisoprene content of at least 92 percent and preferably 94 percent. With reference to FIG. 2 of the drawings, shown is a graphic representation of fluid pressure characteristics with respect to storage cavity displacement for such a bladder 12 unstretched and stretched longitudinally by amounts ranging approximately from 25 to 150 percent. The graph illustrates the results of five laboratory tests on a tubular rubber bladder. Curve 1 represents the fluid pressure characteristics with respect to storage cavity displacement for an unstretched bladder As an unstretched bladder is filled, the pressure of the filling fluid increases rapidly as the bladder initially resists inflating. The pressure peaks and, since hoop stress in the bladder 12 is equal to twice its longitudinal stress, the bladder develops a bulbar aneurism and begins to inflate spherically. The fluid pressure in the bladder 12 then decreases about ten percent, and the inflation proceeds axially. The fluid pressure remains relatively constant during the axial inflation. As the fluid inflates the bladder 12 to about seventy-five percent of its maximum volume, the fluid pressure once again begins to rise and continues to do so, again inflating the bladder 12 in a more radial direction, until the bladder 12 eventually bursts.

Curve II of FIG. 2 represents the fluid pressure characteristics for a bladder 12 longitudinally stretched approximately 25 percent compared to its unstretched length. Curves III, IV and V respectively represent the fluid pressure characteristics for a bladder longitudinally stretched approximately 50 percent, 100 percent and 150 percent compared to its unstretched length. As shown, when a bladder longitudinally stretched to these lengths is inflated with fluid, the response is somewhat similar to that shown by Curve I. There is a rapid rise in pressure, an early pressure peak, forming a spherical bulge in the bladder, a drop in pressure, and then a more gradual rise in pressure.

Figure 7:
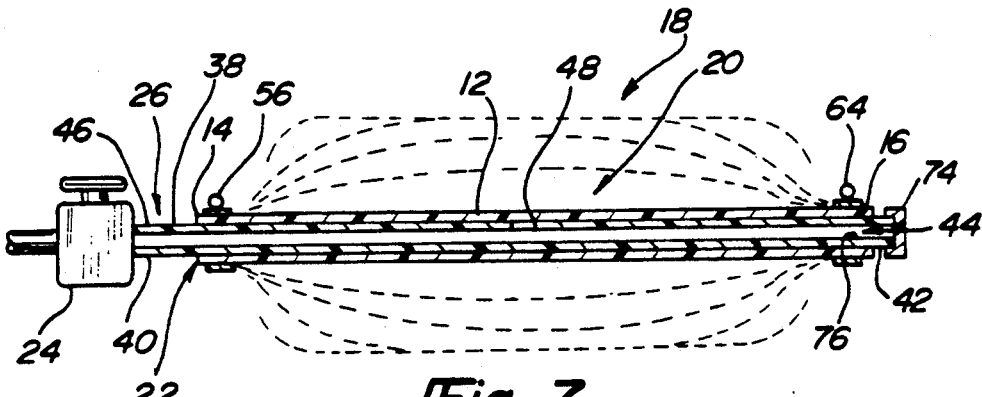
FIG. 7 is a view similar to that of FIG. 6 and illustrates the inflation pattern for a bladder longitudinally stretched by a smaller amount and in empty, partially filled and full states.

The fluid pressure characteristics of a bladder inflated to lengths somewhat below 200 percent compared to unstretched bladder length correspond to an inflation of the bladder 12 as depicted in FIG. 7. As shown, the bladder 12 maintains rather a football shape during a substantial portion of its inflation, the shape of the bladder finally changing to resemble that of a sausage during the latter phase of its inflation.

Figure 3:
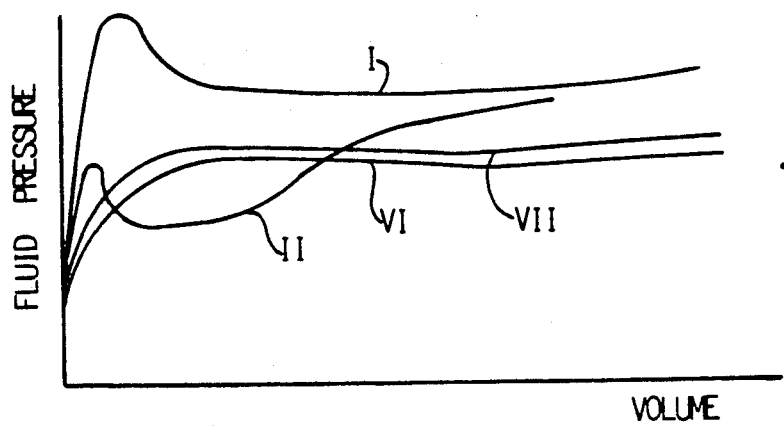
FIG. 3 is a graphic representation of fluid pressure characteristics with respect to storage cavity displacement for a bladder stretched longitudinally by amounts ranging approximately from 150 to 275 percent.

With reference to FIG. 3 of the drawings, shown is a graphic representation of fluid pressure characteristics with respect to storage cavity displacement for a bladder 12 unstretched and stretched longitudinally by amounts ranging approximately from 25 to 275 percent. The graph illustrates the results of four laboratory tests on a tubular rubber bladder. Curve I represents the fluid pressure characteristics with respect to storage cavity displacement for an unstretched bladder, and its fluid pressure characteristics are the same as those previously described for Curve I of FIG. 2.

Curve II of FIG. 3 represents the fluid pressure characteristics for a bladder 12 longitudinally stretched approximately 25 percent compared to its unstretched length, and its fluid pressure characteristics are the same as those previously described for curve II of FIG. 2. Curves VI and VII respectively represent the fluid pressure characteristics for a bladder longitudinally stretched approximately 225 percent and 275 percent compared to its unstretched length. As shown, when a bladder longitudinally stretched to these lengths is inflated with fluid, the response is significantly different from that illustrated by curves previously described.

Figure 6:
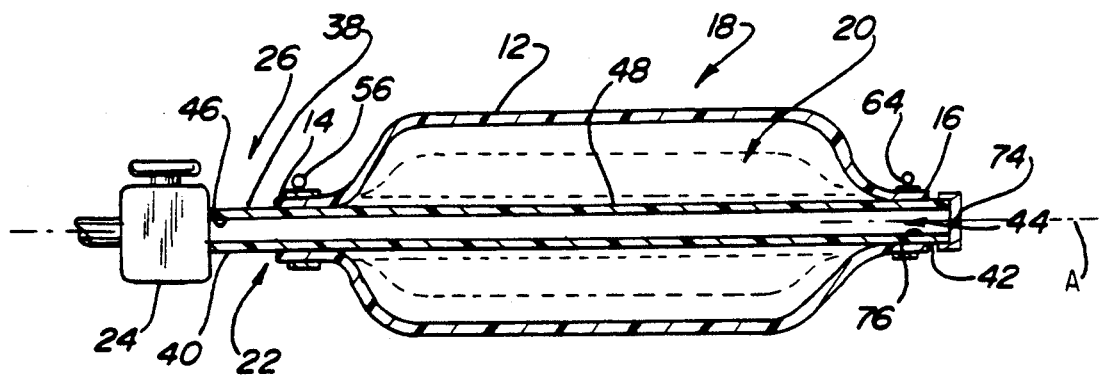
FIG. 6 is a side view, partly in section, of an embodiment of the invention and illustrates the inflation pattern for a bladder longitudinally stretched by a specific amount and in empty, partially filled and full states.

As in previous cases, there is an initial, rapid rise in pressure. An important difference between the fluid pressure characteristics previously described and the ones represented by Curves VI and VII, however, is that no early pressure peak is formed. With the bladder longitudinally stretched by the amounts associated with Curves VI and VII, i.e., approximately 225 and 275 percent respectively compared to its unstretched length, no bulbar aneurism is developed as the bladder begins to inflate. The fluid pressure characteristics of a bladder inflated to lengths near or above 200 percent of its unstretched bladder length correspond to an inflation of the bladder 12 as depicted in FIG. 6. As shown, the bladder maintains a sausage shape throughout substantially all of its inflation.

Eliminating the early pressure peak has an extremely significant consequence. The fluid pressure characteristics illustrated by the curves represent the manner in which the fluid pressure behaves with respect to changes in bladder volume not only when the bladder 12 is being inflated but also when the fluid stored within the bladder 12 is dispensed. This means that, when the bladder 12 is longitudinally stretched by amounts in the range indicated by Curves VI and VII, the fluid will be dispensed at a constant pressure until it is completely exhausted. There will be no sudden increase in pressure when the last of the fluid is being dispensed, and this can be crucial in applications such as intravenous injections. Once the fluid pressure reaches its maximum level, it remains substantially constant throughout the duration of bladder inflation.

It should be noted that another important consequence of stretching the bladder 12 before inflating it is that, as illustrated by Curves II through VII in FIGS. 2 and 3, the maximum fluid pressure is less than that of the unstretched bladder, as shown by Curve I in FIG. 2. This contributes significantly to the number of fill cycles available prior to bladder failure.

Figure 4:
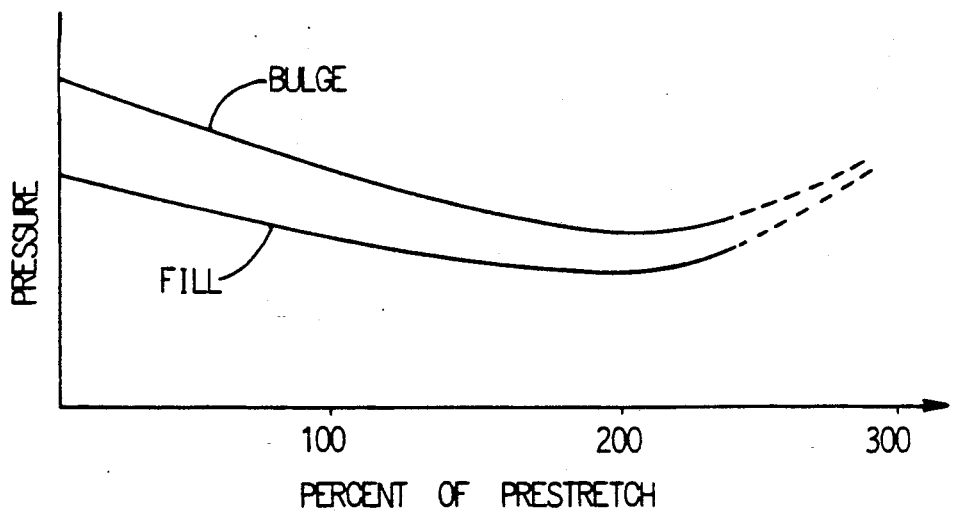
FIG. 4 is a graphic representation of bulge pressure and fill pressure characteristics with respect to bladder stretch.

Shown in FIG. 4 of the drawings is a comparison of the "bulge" pressure, or early pressure peak associated with the formation in the bladder 12 of a bulbar aneurism, with the "fill" pressure associated with the subsequent axial inflation of the bladder 12. The graph shows that, as the amount the bladder 12 is longitudinally stretched with respect to its unstretched length prior to its inflation is increased, the bulge pressure and the fill pressure approach each other asymptotically and remain lower than their initial values.

Figure 5:
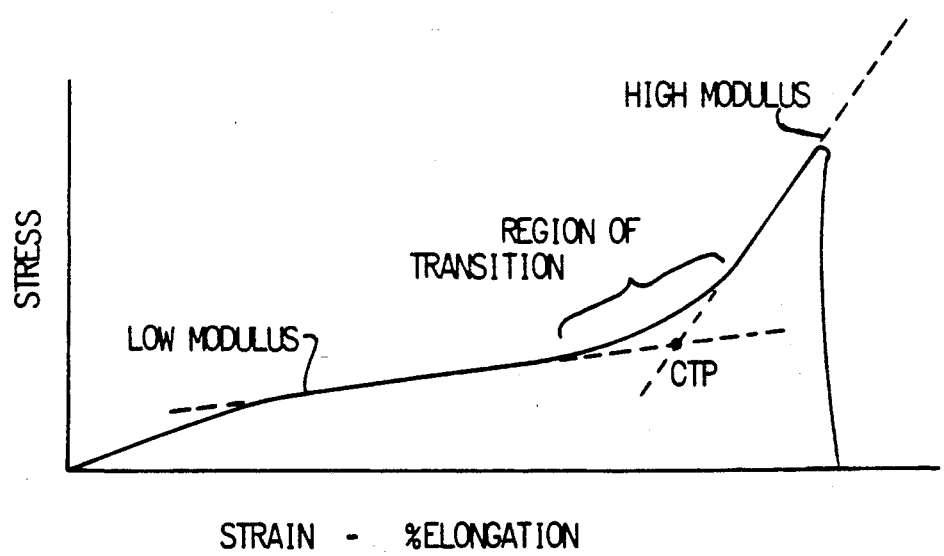
FIG. 5 is a graphic representation of a typical stress-strain curve illustrating the stiffness characteristics with respect to the elongation of an elastic material such as isoprene rubber.

FIG. 5 illustrates the force characteristics with respect to the elongation of a typical elastic material. A property substantially contributing to the desirable performance of the bladder 12 is illustrated by the graph. As shown, the modulus of elasticity, which may be defined as the ratio of the unit stress to the unit deformation of a structural material and which is represented in the graph by the slope of the curve, is substantially constant over nearly half of the curve, undergoes a transition, and is then substantially constant over nearly all of the remaining portion of the curve. This "dual-modulus" characteristic is one of the properties desirable for material used to construct the bladder of the preferred embodiment. The bladder 12 in the preferred embodiment is stretched nearly to or beyond the critical transfer point illustrated in FIG. 5 so that its modulus of elasticity is as represented by the steeper upper portion of the curve.

In the graph, dashed lines representing the two major modulus values have been extended through a point of intersection; and this point has been labelled the CTP (critical transition point). The adjacent area represented by a nonlinear portion of the curve has been labelled the region of transition. This terminology generally corresponds to the terms crystallization point and region of crystallization commonly applied in prevailing explanations of elastic properties.

The modulus of elasticity indicated by the linear portion of the curve prior to the critical transition point is lower than that indicated by the more steeply sloped linear portion of the curve following the point. This means that, initially, an elastic material being stretched would offer relatively low, and constant, resistance. Eventually, however, a proportional limit would be reached, the modulus of elasticity would increase, and the material would thereafter offer a proportionately higher, constant resistance to additional stretching.

This effect is in agreement with a prevailing theory that elastic properties attend materials consisting of long, flexible, chainlike molecules. The resistance offered to elongating forces is initially relatively low. When the chains become nearly taut, however, the resistance, or tensile stress, is significantly increased.

The bladder 12 associated with the fluid pressure characteristics versus storage cavity displacement shown in FIGS. 2, 3 and 4 has an unstretched inside diameter of 5/16 inch, a wall thickness of 1/8 inch, and a length of 8 inches. Bladders having different dimensions may be substituted to provide storage and dispensing apparatuses having different characteristic values of fluid pressure with respect to storage cavity displacement as desired. For example, a bladder having a thicker wall provides a storage and dispensing apparatus having a proportionately higher fluid operating pressure. For a given wall thickness, increasing the inside diameter of the bladder proportionately decreases the fluid operating pressure.

FIGS. 6 and 7 of the drawings show another embodiment of the present invention using a rod 38 for a support 26. The rod 38 extends along the longitudinal axis A of the bladder 12, and a first end 40 of the rod 3 extends through the bladder orifice 22. The first end 14 of the bladder 12 is connected to the rod 38 proximate the first end 40 thereof with a first clamp 56. A second end 42 of the rod 38 is connected to the second end 16 of the bladder 12 with a second clamp 64. The outside diameter of the rod 38 is at least equal to the initial inside diameter of the longitudinally stretched but uninflated bladder 12. The rod 38 has a generally longitudinal lumen 44 having a first opening 46 proximate the first rod end 40 extending through the bladder orifice 22 and at least a second opening 48 proximate the midportion of the fluid storage cavity 20. The lumen 44 may have a third opening 76 proximate the second rod end 42, and this may be closed with a cap 74 or may be connected to a bladder filling device (not shown).

In various embodiments, the rod 38 may serve as an internal bladder support to maintain the bladder 12 in an initially longitudinally stretched condition. It may also serve to facilitate filling and emptying the bladder 12 by virtue of its lumen 44, which provides a fluid path between the first end 40 of the rod 38 extending through the bladder orifice 22 and the fluid storage cavity 20 defined within the bladder 12. By virtue of the fact that the outside diameter of the rod 38 is at least as great as the inside diameter of the longitudinally stretched but uninflated bladder 12, the rod 38 may also serve as a fluid dissipating core to facilitate completely emptying the bladder 12 by ensuring that there is no fluid storage space between the outside surface of the rod 38 and the inside surface of the deflated bladder 12 when the latter is deflated.

Figure 8:
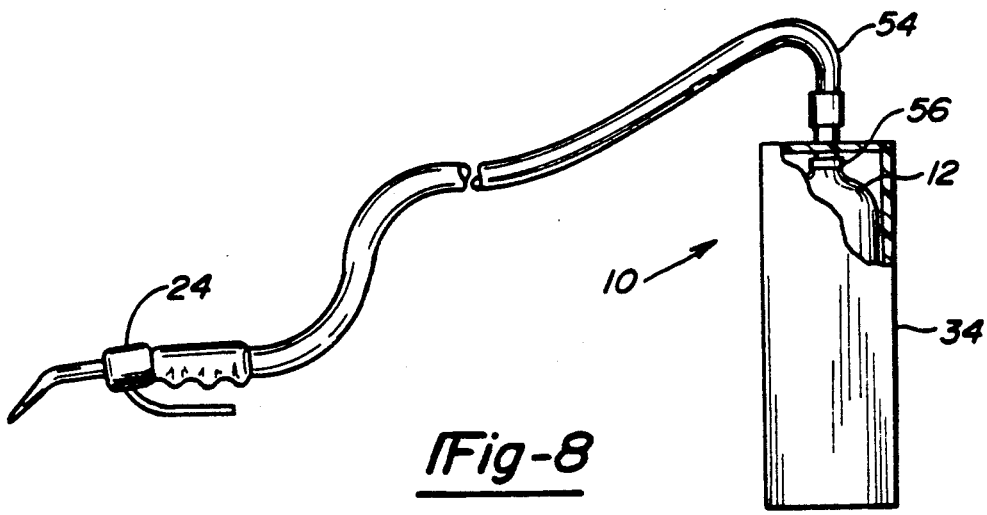
FIG. 8 is a view, partly broken away and in section, of an embodiment of the invention as it might be used in a typical application.

FIG. 8 of the drawings shows an embodiment of the invention as it might be configured for a typical application. The configuration shown is a device suitable for spraying fluids containing insecticide, fertilizer and the like. The embodiment includes a fluid storing and dispensing apparatus 10 having a tubular rubber bladder 12 to store a fluid, a valve 24 to regulate fluid flow from the bladder, and a container 34 that maintains the bladder in a longitudinally stretched condition and restricts its radial inflation to a diameter less than its maximum diameter and expansion limit. A hose 54 is connected between the bladder 12 and the valve 24 to allow positioning the valve 24 for effective spraying without having to move the remainder of the fluid storing and dispensing device 12.

Shown in FIG. 9 is an intravenous injecting device including a tubular rubber bladder 12, which is preferably made of polyisoprene having a cis-polyisoprene content of at least 92 percent and preferably 94 percent. The bladder 12 has a first end 14 and a second end 16. A central region, generally indicated by the reference character 18, is disposed therebetween along a longitudinal axis A. The central region 18 internally defines a fluid storage cavity generally indicated by the reference character 20, and at least one of the ends of the bladder 12 forms an orifice, generally indicated by the reference character 22, therein to admit and/or discharge fluid. A coupling valve 25 is connected to the orifice 22 to retain liquid within the fluid storage cavity 20.

A support, generally indicated by reference character 26, is connected to the bladder 12. The support 26 includes a cylinder 28 having a first end 30 connected to the first end 14 of the bladder 12 and a second end 32 connected to the second end 16 of the bladder. The cylinder 28 forms a container 34 that surrounds the bladder 12 and maintains it longitudinally stretched sufficiently to exhibit post-critical-transition-point pressure-to-volume characteristics. The cylinder has a diameter less than the maximum diameter and expansion limit of the bladder 12 and serves to limit the radial expansion of the bladder 12. The bladder 12 is preferably designed to function in the intravenous injecting device at a pressure of 0.5 pounds per square inch (3.45 kilopascals).

Also shown is an intravenous tube 23 having a tube coupler 27 connected to one end and an injection needle 29 connected to the other end. The tube coupler 27 causes the coupling valve 25 to open when the former is connected to the latter and to close when disconnected. A tube clamp 31 may also be used to prevent fluid flow through the tube 23.

The intravenous injecting device may, of course, be constructed a number of ways, by anyone skilled in the art, to facilitate filling it, transporting it, storing it, maintaining its fluid contents at a relatively constant temperature, and connecting it to various types of intravenous tubes.

To use the intravenous injecting device, the intravenous tube 23 is connected to the device by attaching the tube coupler 27 to the coupling valve 25, and the tube clamp 31 is opened until all gas is expelled, under pressure provided by the expanded bladder 12, from the tube 23 and the injection needle 29. The needle 29 is then inserted into a recipient, and the tube clamp 31 is again opened to allow the fluid contents of the bladder 12 to flow through the tube 23 and the needle 29 into the recipient.

Since the inflated bladder 12 provides all the pressure necessary to force fluid from the bladder 12 into a recipient, the bladder 12 need not be elevated and need not be maintained in any particular orientation. This is an important feature when the device is being used under certain conditions, for example, during a battle in a relatively exposed position.

The bladder 12 is made of polyisoprene having a cis-polyisoprene content of at least 92 percent and preferably 94 percent and is stretched sufficiently to exhibit post-critical-transition-point pressure-to-volume characteristics; therefore, the pressure of the exiting fluid remains substantially constant over the entire range of fluid volume. Since the cylinder 28 diameter is less than the maximum diameter and expansion limit of the bladder 12, it serves to limit the radial expansion of the bladder 12, thereby substantially increasing the number of times the bladder 12 may be reinflated before it fails.

Shown in FIG. 10 is a fluid ejecting device that might be used, for example, by a veterinarian to force a fluid contained therein into a body passage or cavity of an animal being treated. The device includes a tubular rubber bladder 12 having a first end 14 and a second end 16. A central region, generally indicated by the reference character 18, is disposed therebetween along a longitudinal axis A. The central region 18 internally defines a fluid storage cavity generally indicated by the reference character 20.

The first end 14 of the bladder 12 is connected to a nozzle 33 by a first clamp 56; and the second end 16 of the bladder 12 is connected by a second clamp 64 to a rod 38 proximate the second end 42 thereof, the rod 38 extending within the tubular bladder 12 coaxially along the longitudinal axis A. A third clamp 57 disposed between the first end 14 and the second end 16 of the bladder 12 and spaced from the first clamp 56 connects the bladder 12 to the rod 38 proximate a first end 40 thereof, maintaining the bladder 12 in a longitudinally stretched condition. The outside diameter of the rod 38 is at least equal to the initial inside diameter of the longitudinally stretched but uninflated bladder 12. The bladder 12 used in the fluid ejecting device is preferably designed to hold 200 to 2000 milliliters of water.

The rod 38 has a generally longitudinal lumen 44 including a first opening 46 proximate the first end 40 of the rod 38 and at least a second opening 48 proximate the midportion of the fluid storage cavity 20. The lumen 44 may have a third opening 76 proximate the second rod end 42; and this may be connected to a bladder filling device 77 having, for example, a check valve 79 to permit the entry but not the exit of a fluid therethrough. A manually operable tube clamp 31 is disposed on the uninflated portion of the bladder 12 between the first clamp 56 and the third clamp 57 and proximate the nozzle 33 to provide a means for controlling a flow of exiting fluid.

As also shown in FIG. 10, the fluid ejecting device may be fitted with a shoulder strap 35 to facilitate its operation, especially under conditions where one or both hands of an operator must be free to position the nozzle 33. One end of the shoulder strap 35 may typically be attached to the fluid ejecting device proximate the second clamp 64; and the other end attached proximate the third clamp 57, the shoulder strap thus being stably positioned to span that portion of the fluid ejecting device representing the majority of its weight.

It would be obvious to anyone skilled in the art that the fluid ejecting device may be constructed in many different ways and in many different configurations. For example, the bladder 12 may be filled and evacuated at the same end, and the device may be enclosed in a suitable container to maintain the bladder 12 in a stretched condition and to meet both practical and aesthetic requirements. The device may even be made to function as a toy water ejecting device when configured as previously described or especially if it is enclosed in a container configured to simulate a pistol, rifle, bazooka or the like having a trigger-like mechanism to release the water.

To use the fluid ejecting device, the bladder 12 is filled with fluid, for example, by connecting the bladder filling device 77 to a source (not shown) of pressurized fluid. The fluid flows through the third lumen opening 76, through the lumen 44, and through the second lumen opening 48 into the fluid storage cavity 20. Once filled, the fluid ejecting device can be operated by inserting the nozzle 33 in the appropriate body passage or cavity an animal undergoing treatment and releasing the tube clamp 31.

The bladder 12 is made of polyisoprene having a cis-polyisoprene content of at least 92 percent and preferably 94 percent and is stretched sufficiently to exhibit post-critical-transition-point pressure-to-volume characteristics; therefore, the pressure of the exiting fluid remains substantially constant over the entire range of fluid volume. Since the outside diameter of the rod 38 is at least as great as the inside diameter of the longitudinally stretched but uninflated bladder 12, the rod 38 may also serve as a fluid dissipating core to facilitate completely emptying the bladder 12 by ensuring that there is no fluid storage space between the outside surface of the rod 38 and the inside surface of the deflated bladder 12 when the latter is deflated.

Figure 11:
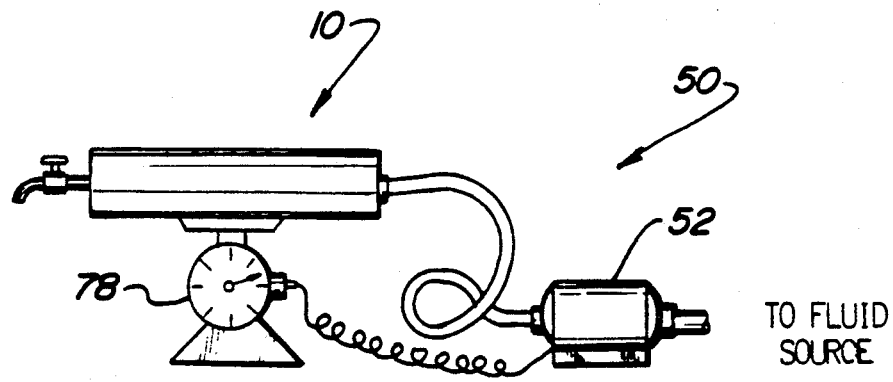
FIG. 11 is a view of still another embodiment of the invention.

With reference to FIG. 11 of the drawings, shown is a replenishing fluid storing and dispensing system generally indicated by reference character 50. The system includes the fluid storing and dispensing apparatus generally indicated by reference character 10, a sensing device such as a weight scale 78 to sense the amount of fluid stored in the storage apparatus 10, and a pump 52 to transfer fluid from a source thereof to the storage apparatus 10.

Figure 12:
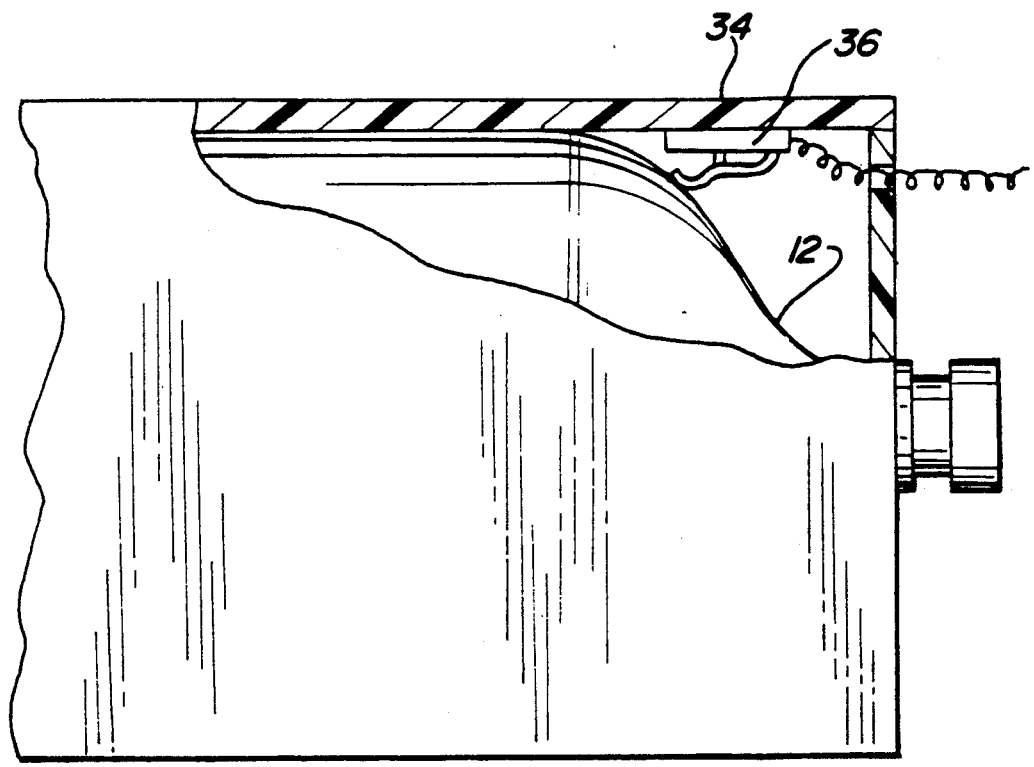
FIG. 12 is a fragmented view, partly in section, illustrating a detail of the embodiment of the invention shown in FIG. 11.

FIG. 12 of the drawings shows a sensing switch 36 mounted to the container 34 to position it proximate the bladder 12. The sensing switch 36 may typically be a bistable device that is transferred to a first state when the bladder 12 is inflated beyond a minimum amount and transferred to a second state when the bladder 12 is deflated below a minimum amount. The sensing switch 36 may be readily incorporated into an electrical circuit (not shown) designed, for example, to maintain the fluid stored in the bladder 12 between desired limits. The pump 52 is responsive to the state of the sensing switch 36 and transfers fluid from the source to the bladder 12 whenever the amount of fluid remaining in the bladder 12 is reduced below a desired minimum and stops transferring fluid whenever the amount of fluid in the bladder 12 exceeds a desired maximum.

The bladder 12 may be made from commonly available rubber tubing such as that produced from natural rubber or produced synthetically to obtain desired characteristics. In the preferred embodiment, the rubber is polyisoprene, which is called "natural rubber," having a cis-polyisoprene content of at least 92 percent and preferably 94 percent. In tests, this material was found to be the most acceptable. Such material is relatively chemically inert and impermeable with respect to fluids that might commonly be stored in the bladder 12 and also with respect to ambient elements such as oxygen.

As is typical of polymers, polyisoprene molecules are composed of long chains of molecules, or monomers, the chains of natural rubber having an average length of 5000 isoprene units. The elastic properties of polymers may be viewed in terms of their structure. In a sample of material, the long polymer chains are typically coiled and intertangled. When a stretching force is applied, the long polymer chains become elongated; and the material appears to "flow" in the direction of the applied force.

The molecular configuration of an isoprene monomer is as follows.

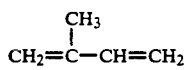

The molecular configuration of cis-1,4 addition polyisoprene is as follows.

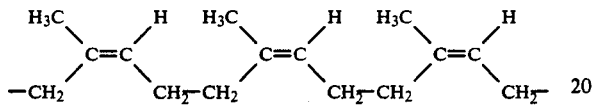

Chemically bonding, referred to as cross-linking, the polymer chains can reduce the relative movement of the chains. When a stretching force applied to a cross-linked network is removed, the elongated polymer chains return to their original coiled state. Cross-linked polymers that exhibit such elastic properties are referred to as elastomers.

Bonding the polymer chains at average intervals of about 100 to 1000 bonds along each chain enables the polymer to be stretched to several times its rest length without breaking. The number of cross-links between the polymer chains of an elastomer is directly proportional to its resistance to stretching.

One of the major problems associated with natural rubber is tackiness. A vulcanization process, using sulfur to form cross-links between the polyisoprene chains, was developed (by Charles Goodyear circa 1839) to solve the tackiness problem; and vulcanization was also subsequently used to form the cross-links that provide the preferred measure of elasticity.

The molecular configuration of sulfur cross-linked cis-1,4 addition polyisoprene is as follows.

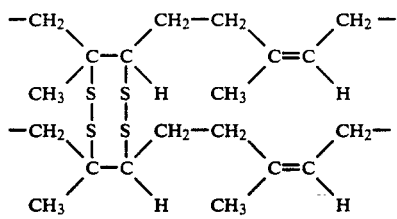

As previously mentioned, polyisoprene is the preferred material for making the bladder 12 of this invention; however, it should be understood that the term "rubber," as used in the claims, is not limited to polyisoprene and includes other materials having similar desirable properties. Neoprene may also be used for certain applications, the neoprene being compounded using substantially less carbon black than that commonly used, for example, in engine mounts and shock absorbers.

The molecular configuration of chloroprene, 2-chloro-1,3-butadiene, the monomer from which all neoprenes are made, is as follows.

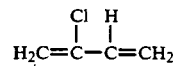

The degree of crystallinity in a neoprene is substantially a function of the amount of trans configuration in the polymer. If the amount of trans configuration is increased, the degree of crystallinity is also increased.

The molecular configuration of trans-1,4-addition poly-2-chloro-1,3-butadiene neoprene is as follows.

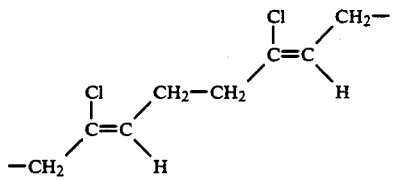

Since the bladder 12 may be made from a commonly available material and the other elements of the fluid storing and dispensing apparatus may also be easily made or obtained from readily available sources, the apparatus can be fabricated easily, inexpensively and in forms tailored for specific applications.

An ideal application for the preferred embodiment of the invention described would be as a beverage dispensing device or the like. In such applications, where constant fluid pressure with respect to bladder volume over a complete duty cycle is not critical, an unstretched or partially stretched bladder may be used; however, a stretched bladder is preferred for reusable dispensing devices.

With reference to FIG. 13, shown is an embodiment of such a beverage dispensing device generally indicated by the reference character 110. The device includes an elongated, elastic bladder 112, insulating material 114, a valve mechanism 116, and a housing 118. The insulating material 114 is disposed within the housing 118, and the bladder 112 is substantially encased within the insulating material 114. The valve mechanism 116 is secured by a clamp 122 to a first end of the elongated bladder 112, the second end of which is closed by another clamp 128 or the like.

Mounted within the housing 118 is a collar 130 that secures the first end of the bladder 112 to the housing 118. Also mounted within the housing 118 are support members 120 that secure the second end of the bladder 112 to the housing 118. The elastic bladder 112 has an initial, unexpanded shape approximately indicated by dashed lines 124, a partially expanded shape approximately indicated by dotted lines 126, and a fully expanded shape approximately indicated by the solid lines illustrating the bladder 112. The insulating material 114 has an outer configuration conforming to the inside shape of the housing 118 and an inner configuration conforming to the outer shape of the expanded bladder 112. The housing 118 and the insulating material 114 thus cooperate to support the bladder 112 when the latter is expanded. The overall dimensions of the housing may be conveniently chosen for specific applications such as storing carbonated beverages in a home refrigerator.

The housing 118 has a removable portion 132 frangibly attached thereto with, for example, a perforated section of housing material, a tear-away paper band, removable tape or the like. With the portion 132 in place, the valve mechanism 116 is protectively confined and isolated from contaminants and physical abuse. With the portion 132 removed (as shown in FIGS. 12, 13 and 14), the valve mechanism 116 is accessible for easy operation.

The valve mechanism 116 has a body that defines a channel (not shown) for conducting an exiting flow away from the bladder 112 and that connects the valve mechanism 116 to the bladder 112. The valve mechanism 116 also has a valve seat (not shown) formed, and a valve member effectively disposed, therewithin. A valve operating member 134 is mounted in the body of the valve mechanism 116 for positioning the valve member with respect to the associated valve seat, the valve mechanism 116 normally inhibiting an exiting flow of the fluid stored within the bladder 112 when the valve member is positioned against the valve seat and allowing an exiting flow when the valve member is positioned away from the valve seat, the rate of flow being a function of the distance between the valve member and the valve seat.

FIG. 17 is another embodiment of the dispensing device similar to that shown in FIG. 13 and is generally indicated by reference character 136. The device includes an elongated, elastic bladder 112, insulating material 114, a valve mechanism 116, and a housing 138. The insulating material 114 is disposed within the housing 138, and the bladder 112 is substantially encased within the insulating material 114. The valve mechanism 116 is secured by a clamp 122 to a first end of the elongated bladder 112, the second end of which is closed by another clamp 128 or the like.

Mounted within the housing 138 are support members 120 and 140 that secure the bladder 112 within the housing 138. The insulating material 114 has an outer configuration conforming to the inside shape of the housing 138 and an inner configuration conforming to the outer shape of the expanded bladder 112. The housing 138 and the insulating material 114 cooperate to support the bladder 112 when the latter is expanded.

FIG. 17 shows the dispensing device 136 with the first end of the bladder 112 folded within the housing 138. This provides the valve mechanism 116 with protection from physical abuse and with isolation from contaminants. The housing 138 has end flaps 142 that open outwardly, as shown in FIG. 18, to permit the valve mechanism 116 to be withdrawn from the confines of the housing 138 to an operably accessible position. Each of the end flaps 142 has a removable, semicircular portion 144 frangibly attached thereto with, for example, a perforated section of flap material or the like. With each of the semicircular portions 144 removed and the valve mechanism 116 withdrawn from the housing 138, the end flaps 142 may be closed. A pair of collars 146 are attached to the valve mechanism 116 to receive the end flaps 142 therebetween so that the valve mechanism 116 extends through the circular opening in the end flaps 142 left by the removed semicircular portions 144 and is supported by the end flaps 142. The valve mechanism 116 is constructed and, once withdrawn from the housing and secured by the end flaps 142, operates as previously described in relation to the dispensing device 110 shown in FIG. 13.

FIG. 19 shows yet another embodiment of the dispensing device, again similar to that shown in FIG. 13, and is generally indicated by reference character 148. The device includes an elongated, elastic bladder 112, insulating material 114, a valve 150, and a housing 152.

The insulating material 114 is disposed within the housing 152, and the bladder 112 is substantially encased within the insulating material 114. The valve 150 is secured by a clamp 122 to a first end of the elongated bladder 112, the second end of which is closed by another clamp 128 or the like.

The insulating material 114 has an outer configuration conforming to the inside shape of the housing 152 and an inner configuration conforming to the outer shape of the expanded bladder 112. The housing 152 and the insulating material 114 cooperate to support the bladder 112 when the latter is expanded.

Mounted within the housing 152 are support members 120 that secure the second end of the bladder 112 within the housing 152. A portion of the first end of the bladder 112 extends through and is supported and laterally restricted by a pair of fixed collars 154 secured by a support member 156 mounted within the housing 152. A pair of collars 146 are effectively attached to the valve 150. The collars 146 are secured by a support member 158, which is slidably mounted within the housing 152.

After the bladder 112 has been filled, the support member 158 is positioned proximate the support member 156, retracting the valve 150 to a protected position (indicated by broken lines and reference character 150') within the housing 152. The portion 113 of the bladder 112 disposed between the collars 154 and 146 is forced into a folded configuration (indicated by broken lines and reference character 113'). The portion 113 of the bladder 112 disposed between the collars 154 and 146 may be covered by a flexible but substantially nonexpandable sleeve 115, made of any of a number of well-known materials, to prevent the portion 113 from expanding when the bladder 112 is being filled.

The housing 152 has an end flap 160 that opens outwardly to provide access to the nozzle 150. The support member 158 has finger holes 159 disposed therein to enable a user to grasp the support member 158 and pull it away from the support member 156 to a position where the nozzle 150 protrudes from the housing 152. The end flap 160 has a restraining member, or tab, 162 insertable in a slot 161 in the support member 158 to secure the flap 160 when in a closed position. The end flap 160 also has a generally central portion 163 that may be torn away to provide an aperture through which the valve 150 extends when the flap 160 is closed.

With reference to FIGS. 20a, 20b and 21b, shown are two additional embodiments of the dispensing device, again similar to that shown in FIG. 13, and generally indicated by reference character 164. The devices each include an elongated, elastic bladder 112, insulating material 114, a first valve mechanism 166, and a housing 168. The insulating material 114 is disposed within the housing 168, and the bladder 112 is substantially encased within the insulating material 114. The first valve mechanism 166 is secured by a clamp 122 to a first end of the elongated bladder 112 and is also mounted through an end of the housing 168.

The first valve mechanism 166 has a body that defines a channel (not shown) for conducting an exiting flow away from the bladder 112 and that connects the first valve mechanism 166 to the bladder 112. The first valve mechanism 166 also has a valve seat (not shown) formed, and a valve member effectively disposed, therewithin. The valve member is normally positioned against the valve seat, causing the first valve mechanism 166 to inhibit an exiting flow of the fluid stored within the bladder 112.

A second valve mechanism 170 is shown in FIG. 20 and has a body that defines a channel (not shown) for conducting an exiting flow away from the bladder 112 and that connects the second valve mechanism 170 to the first valve mechanism 166. The second valve mechanism 170 also has a valve seat (not shown) formed, and a valve member effectively disposed, therewithin.

As shown in FIG. 20a, the second valve mechanism 170 has a release member extending therefrom that positions the valve member within the first valve mechanism 166 away from the associated valve seat when the second valve mechanism 170 is connected to the first valve mechanism 166 as shown in FIG. 20b. This permits the second valve mechanism 170 to have exclusive control over an exiting flow.

A valve operating member 172 is mounted in the body of the second valve mechanism 170 for positioning the valve member disposed therein with respect to the associated valve seat, the second valve mechanism 170 normally inhibiting an exiting flow of the fluid stored within the bladder 112 when the valve member is positioned against the valve seat and allowing an exiting flow when the valve member is positioned away from the valve seat, the rate of flow being a function of the distance between the valve member and the valve seat.

FIG. 21 also shows a dispensing device 164 having a first valve mechanism 166 secured by a clamp 122 to a first end of the elongated bladder 112 and also mounted through an end of the housing 168. The first valve mechanism 166 has a body that defines a channel (not shown) for conducting an exiting flow away from the bladder 112 and that connects the first valve mechanism 166 to the bladder 112. The first valve mechanism 166 also has a valve seat (not shown) formed, and a valve member effectively disposed, therewithin. The valve member is normally positioned against the valve seat, causing the first valve mechanism 166 to inhibit an exiting flow of the fluid stored within the bladder 112.

A second valve mechanism 174 is shown in FIG. 21 and has a body that defines a channel (not shown) for conducting an exiting flow away from the bladder 112 and that connects the second valve mechanism 174 to the first valve mechanism 166. The second valve mechanism 174 also has a valve seat (not shown) formed, and a valve member effectively disposed, therewithin.

The body of the second valve mechanism 174 has a release member extending therefrom that positions the valve member within the first valve mechanism 166 away from the associated valve seat when the second valve mechanism 174 is connected to the first valve mechanism 166. This permits the second valve mechanism 174 to have exclusive control over an exiting flow.

A valve operating member 176 is mounted in the body of the second valve mechanism 174 for positioning the valve member disposed therein with respect to the associated valve seat, the second valve mechanism 174 normally inhibiting an exiting flow of the fluid stored within the bladder 112 when the valve member is positioned against the valve seat and allowing an exiting flow when the valve member is positioned away from the valve seat, the rate of flow being a function of the distance between the valve member and the valve seat.

The second valve mechanism 174 is similar to that 170 shown in FIG. 20 but is made suitable for generally vertical mounting through a horizontal surface (for example, a counter top) by having an extended neck portion 178 for providing sufficient clearance to position a receptacle for receiving an exiting flow. The second valve mechanism 174 also has an extended tube 180, which may be flexible, for connecting to a remotely located bladder 112.

Figure 22:
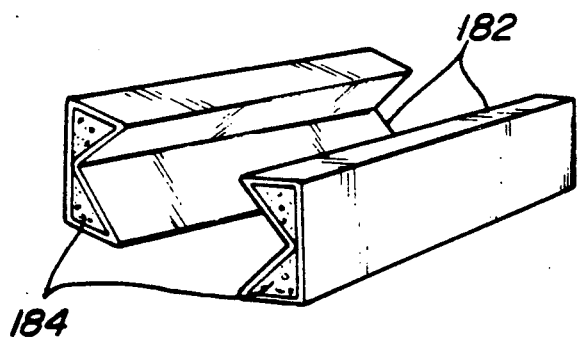
FIGS. 22 through 27 are perspective views of various container and insulation configurations associated with additional embodiments of the invention.

FIGS. 22 through 27 show perspective views of various container and insulation configurations associated with additional embodiments of the invention. FIG. 22 shows a pair of members 182 formed of folded material, such as corrugated cardboard, the enclosed spaces being fillable with an insulating material 184, the members 182 cooperating to provide both insulation and mechanical support for a bladder (not shown).

Figure 23:
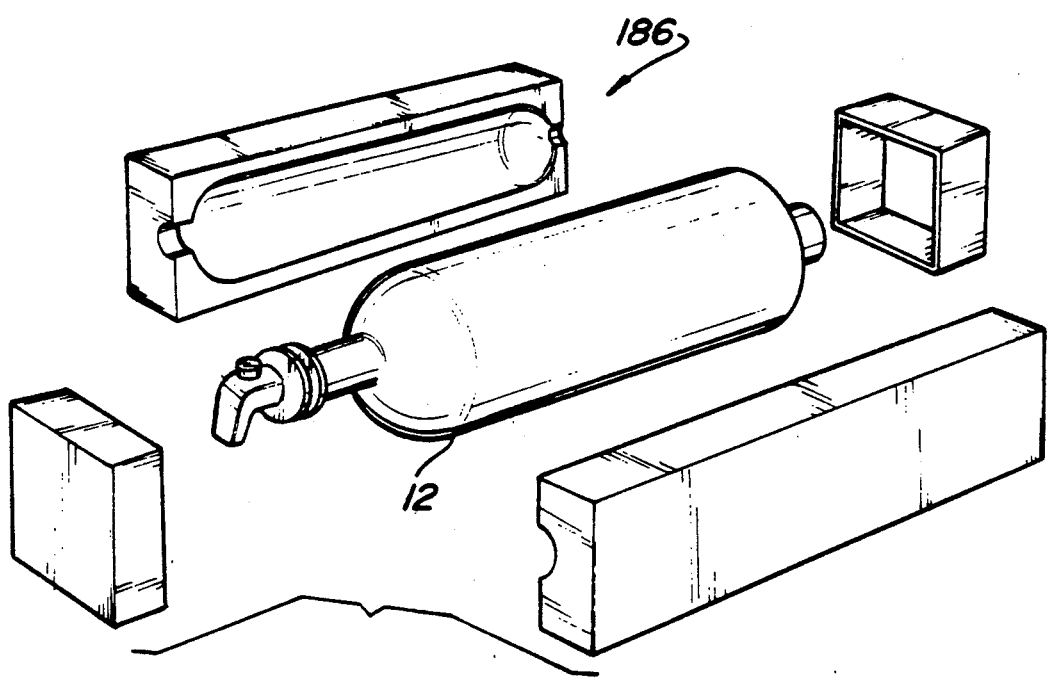
Figure 24:
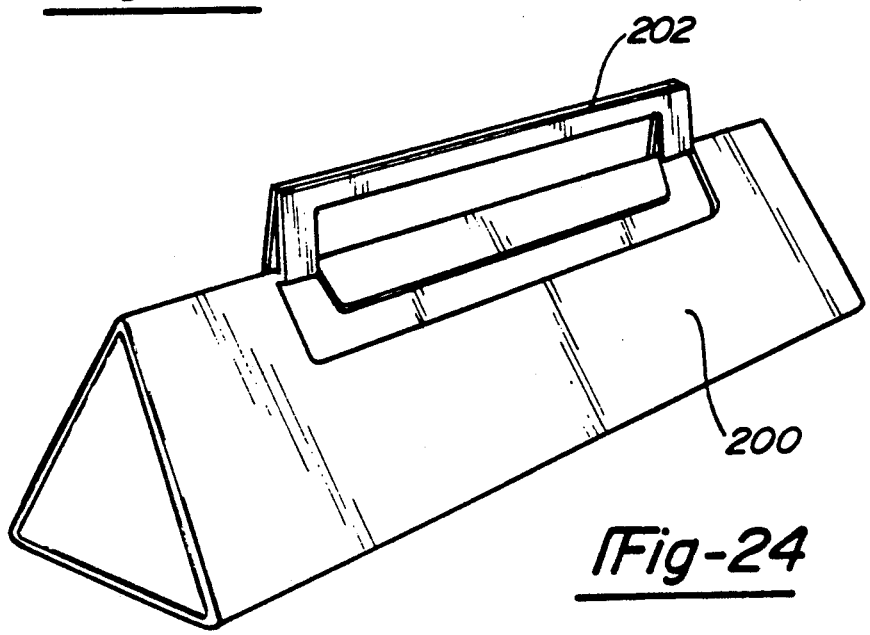

FIG. 23 shows a container, generally indicated by reference character 186, formed of an insulating material to provide both insulation and mechanical support for a bladder 112. The combination may be inserted into a separate housing or may be assembled to form a complete unit by itself. FIG. 24 shows a housing 200 formed of a material such as corrugated cardboard and having carrying handles 202 that fold out of the housing 200. The shape of the housing 200 provides stability when the device is residing on a generally horizontal surface, and, when the handles are folded, the shape facilitates stable stacking when alternate layers of the housings 200 are inverted.

Figure 25:
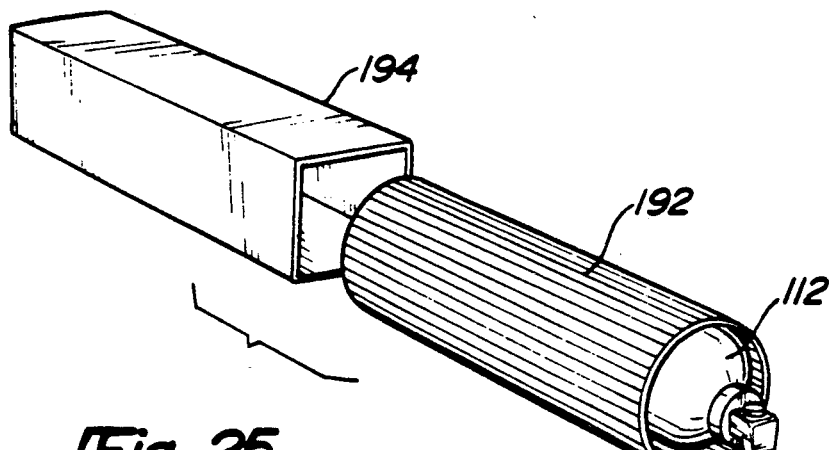
Figure 26:
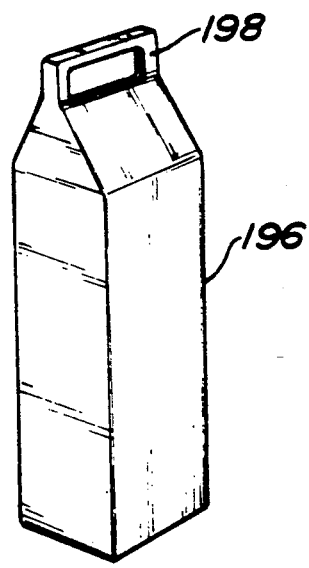
Figure 27:
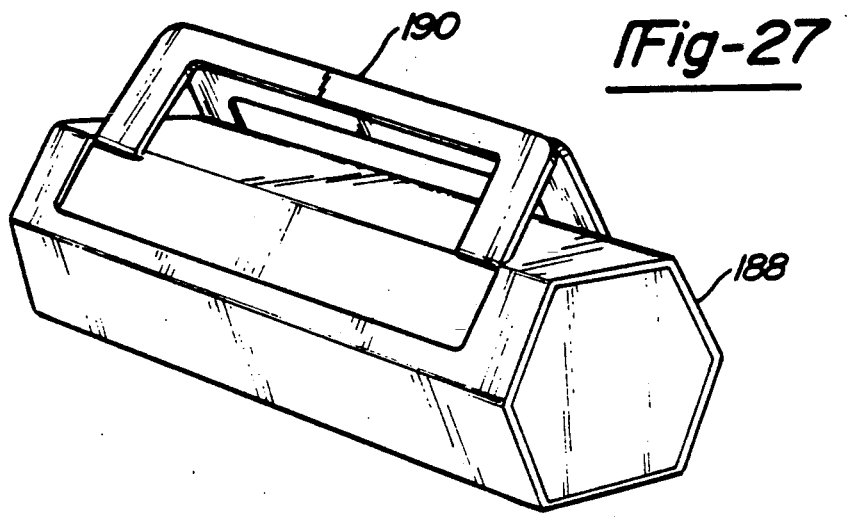

The configuration shown in FIG. 25 has insulating material 192 formed in a circular cylinder to surround a bladder 112, the insulation being encased within a rectangular housing 194. FIG. 26 shows a housing 196 designed for vertical storage and carrying and having handles 198 disposed to facilitate the latter. Shown by FIG. 27 is a hexagonally shaped housing 188, representing a space-saving and material-saving configuration, being formed of material such as corrugated cardboard and having carrying handles 190 that fold out of the housing 188.

Any of the previously described embodiments may be constructed of a variety of materials. As mentioned, the housings may be formed of corrugated cardboard and contain insulating material or be formed of insulating material. The insulating material may be any known material that inhibits thermal conduction and convection, it may be any known reflective material that reflects thermal radiation, or it may be a combination of both materials.

To be suitable for storing and dispensing consumable beverages, however, the bladder 112 must not only maintain a liquid under pressure but also maintain its taste, its purity and, commonly, its carbonation for extended periods. The material forming the bladder 112 must, therefore, be one that not only stores and dispenses beverages while maintaining a constant beverage pressure but that also ensures the lasting quality of the beverage stored therewithin. To do this, it must be chemically inert and impermeable with respect to the elements contained in the beverage and also with respect to ambient elements, such as oxygen.

With reference to FIG. 13, shown is an embodiment of the beverage dispenser physically described previously. Briefly, the device includes an elongated, elastic bladder 112, insulating material 114, a valve mechanism 116, and a housing 118. When empty, the elastic bladder 112 has an initial, unexpanded shape approximately indicated by dashed lines 124. As liquid is introduced under pressure, the bladder 112 expands spherically about an axially local point until the lateral dimension of the bladder 112 has reached its predetermined maximum. Thereafter, the expanding portion proceeds to grow axially until the entire effective length of the bladder 112 has been expanded.

As the volume of the bladder 112 increases, the beverage pressure behaves essentially as represented by Curve I of the graph illustrated in FIG. 2. Before any liquid is introduced, the pressure within the bladder 112, as shown, is zero. As liquid is forced into the bladder 112, the pressure increases rapidly as the bladder 112 initially resists expanding. The pressure peaks and, since hoop stress in the bladder 12 is equal to twice its longitudinal stress, the bladder develops a bulbar aneurism and begins to inflate spherically. The fluid pressure in the bladder 12 then decreases about ten percent, and the inflation proceeds axially. The fluid pressure remains relatively constant during the axial inflation. As the fluid inflates the bladder 12 to about seventy-five percent of its maximum volume, the fluid pressure once again begins to rise and continues to do so, again inflating the bladder 12 in a more radial direction, until the bladder 12 eventually bursts. As indicated, however, the pressure remains relatively constant over a substantial portion of the range of bladder volume.

As liquid is dispensed from the bladder 112, the latter contracts in a manner and sequence essentially reverse to that of its expansion. The result is that nearly an entire volume of liquid may efficiently be dispensed under the influence of a reasonably constant pressure.

If desired, simple modifications may be introduced to extend the constant portion of the pressure-versus-volume relationship of the device. For example, a member having a bulbous portion may be disposed within the bladder 112 to prestress the bladder by imparting an initial spherical shape thereto and thus significantly reduce the pressure rise time and the initial pressure peak shown by Curve I of the graph shown in FIG. 2.

Many changes and modifications may be made to the details of the previously described device without departing from the nature and spirit of the invention. Accordingly, it is to be understood that the invention is not limited to those details but is defined by the appended claims.

What is claimed is:

1. A fluid storing and dispensing apparatus comprising:
    a tubular rubber bladder having first and second ends and a central region therebetween disposed along a longitudinal axis, the central region defining a fluid storage cavity and at least one of the ends forming an orifice therein to admit and/or discharge fluid therethrough, the bladder having a first, and substantially constant, modulus of elasticity when longitudinally stretched within a first range of elongation and a second, greater, and substantially constant, modulus of elasticity when longitudinally stretched within a second, higher, range of elongation, the second range of elongation beginning at a point greater than 200 percent of the unstretched bladder length;
    valve means for regulating the flow of fluid through the bladder orifice; and
    a support connected to the bladder at its first and second ends, the support and the bladder cooperating to maintain the bladder initially longitudinally stretched by an amount within the second range of elongation to provide a substantially constant fluid pressure with respect to the displacement of the fluid storage cavity.

2. The apparatus according to claim 1, further comprising a container surrounding the bladder and having a diameter less than the maximum diameter and expansion limit thereof to limit lateral deformation produced in the bladder and thereby increase the number of fill cycles prior to bladder failure.

3. The apparatus according to claim 2, wherein the bladder is made of polyisoprene.

4. The apparatus according to claim 3, wherein the bladder material has a cis-1,4 addition polyisoprene content of at least 92 percent.

5. The apparatus according to claim 2, wherein the bladder is made of neoprene.

6. The apparatus according to claim 5, wherein the bladder material is trans-1,4 addition poly-2-chloro-1,3-butadiene.

7. The apparatus according to claim 2, wherein the support comprises a rod extending along the longitudinal axis of the bladder, one end of the rod extending through the bladder orifice.

8. The apparatus according to claim 7, wherein the outside diameter of the rod is at least equal to the initial inside diameter of the stretched but uninflated bladder.

9. The apparatus according to claim 8, wherein the rod forming the support has therein a generally longitudinal lumen having an opening proximate the rod end extending through the bladder orifice and at least one opening proximate the midportion of the fluid storage cavity.

10. The apparatus according to claim 9, further comprising:
    sensing means for measuring the fluid in the bladder to produce an output signal representative of the fluid quantity; and
    a pump to transfer fluid from a source thereof to the bladder in response to the output signal produced by the sensing means when the quantity of fluid in the bladder drops below a specific amount.

11. The apparatus according to claim 10, wherein the sensing means comprises a sensing switch actuatable in response to a specific amount of expansion of the bladder.

12. The apparatus according to claim 2, wherein the support comprises a supporting member disposed outside the bladder.

13. The apparatus according to claim 12, wherein the support comprises the container and is a cylinder having a first end connected to the first end of the bladder and having a second end connected to the second end of the bladder.

14. The apparatus according to claim 13, further comprising support members disposed in the spaces defined proximate the ends of the bladder and between the fully inflated bladder and the container.

15. The apparatus according to claim 14, further comprising:
    sensing means for measuring the fluid in the bladder to produce an output signal representative of the fluid quantity; and
    a pump to transfer fluid from a source thereof to the bladder in response to the output signal produced by the sensing means when the quantity of fluid in the bladder drops below a specific amount.

16. The apparatus according to claim 15, wherein the sensing means comprises a weight scale that responds to the weight of the fluid stored in the bladder by producing an output signal representative of the weight.

17. A method for storing and dispensing fluids, the method comprising the steps of:
- providing a tubular rubber bladder having first and second ends and a central region therebetween disposed along a longitudinal axis, the central region defining a fluid storage cavity and at least one of the ends forming an orifice therein to admit and/or discharge fluid therethrough, the bladder having a first, and substantially constant, modulus of elasticity when longitudinally stretched within a first range of elongation and a second, greater, and substantially constant, modulus of elasticity when longitudinally stretched within a second, higher, range of elongation;
- providing a valve connected to the orifice to regulate a flow of fluid therethrough;
- providing a support connectable to the bladder;
- stretching the bladder longitudinally by an amount within the second range of elongation to provide a substantially constant fluid pressure with respect to the displacement of the fluid storage cavity, the second range of elongation beginning at a point greater than 200 percent of the unstretched bladder length;
- connecting the bladder at its first and second ends to the support to maintain the bladder in its longitudinally stretched condition;
- filling the bladder with fluid; and
- operating the valve to controllably dispense the fluid.

18. A method for storing, dispensing and replenishing a fluid, the method comprising the steps of:
- providing a tubular rubber bladder having first and second ends and a central region therebetween disposed along a longitudinal axis, the central region defining a fluid storage cavity therein wherein at least one of the ends forms an orifice therein to admit and/or discharge fluid therethrough, the bladder having a first, and substantially constant, modulus of elasticity when longitudinally stretched within a first range of elongation and a second, greater, and substantially constant, modulus of elasticity when longitudinally stretched within a second, higher, range of elongation;
- providing a valve connected to the orifice to regulate the flow of fluid therethrough;
- providing a support connectable to the bladder;
- stretching the bladder longitudinally by an amount within the second range of elongation to provide a substantially constant fluid pressure with respect to the displacement of the fluid storage cavity, the second range of elongation beginning at a pointing greater than 200 percent of the unstretched bladder length;
- connecting the bladder at its first and second ends to the support to maintain the bladder in its longitudinally stretched condition;
- providing a sensor to measure the amount of fluid in the bladder;
- providing a pump to transfer fluid from a source thereof to the bladder;
- sensing the amount of fluid remaining in the bladder; and
- pumping fluid from the source thereof to the bladder whenever the amount of fluid remaining in the bladder falls below a specific amount.

19. A fluid storing and dispensing apparatus comprising:
- an elastic, tubular bladder for storing beverages requiring pressurized storage and chemical isolation, the bladder being formed of a material that is substantially chemically inert and impermeable, the bladder extending along a longitudinal axis and, upon the introduction of a beverage thereinto, maintaining a generally constant fluid pressure independent of bladder volume as the bladder expands and, upon the dispensing of the beverage therefrom, maintaining a generally constant fluid pressure independent of bladder volume as the bladder contracts, the bladder having a first, and substantially constant, modulus of elasticity when longitudinally stretched within a first range of elongation and a second, greater, and substantially constant, modulus of elasticity when longitudinally stretched within a second, higher, range of elongation, the bladder being stretched longitudinally by an amount within the second range of elongation, the second range of elongation beginning at a point greater than 200 percent of the unstretched bladder length;
- insulating means for retarding changes in the temperature of a stored beverage; and
- a first valve mechanism connected to the bladder for selectively retaining and controlling an exiting flow of the beverage stored within the bladder.

20. The apparatus according to claim 19, further including a housing for encasing the bladder and the insulating means.

21. The apparatus according to claim 20, wherein a portion of the housing encasing the valve mechanism is frangibly attached to the remaining part of the housing for providing convenient access to the valve mechanism.

22. The apparatus according to claim 20, wherein the housing encases and supports the bladder and the insulating means.

23. The apparatus according to claim 22, wherein the housing encases and supports the valve mechanism.

24. The apparatus according to claim 22, further including a housing for encasing the bladder, the housing being formed of an insulating material for retarding changes in the temperature of a stored beverage.

25. The apparatus according to claim 24, wherein the bladder is made of polyisoprene.

26. The apparatus according to claim 25, wherein the bladder material has a cis-1,4 addition polyisoprene content of at least 92 percent.

27. The apparatus according to claim 24, wherein the bladder is made of neoprene.

28. The apparatus according to claim 27, wherein the bladder material is trans-1,4 addition poly-2-chloro-1,3-butadiene.

29. The apparatus according to claim 20, further including a second valve mechanism operatively connectable to the first valve mechanism for selectively retaining or controlling an exiting flow of the beverage stored within the bladder.

30. A fluid storing and dispensing apparatus comprising:
- an elastic, tubular bladder for storing beverages requiring pressurized storage and chemical isolation, the bladder being formed of a material that is substantially chemically inert and permeable, the bladder extending along a longitudinal axis, the bladder being stretched from 25 to 200 percent of its unstretched bladder length and, upon the introduction of a beverage thereinto, maintaining a generally constant fluid pressure independent of bladder volume as the bladder expands and, upon the dispensing of the beverage therefrom, maintaining a generally constant fluid pressure independent of bladder volume as the bladder contracts;

insulating means for retarding changes in the temperature of a stored beverage;

a first valve mechanism connected to the bladder for selectively retaining and controlling an existing flow of the beverage stored within the bladder;

a housing for encasing and supporting the bladder and the insulating means;

a support member mounted within the housing;

a fixed collar secured to the support member within the housing and surrounding the bladder at a preselected distance from an end thereof used for dispensing the beverage stored within the bladder, thereby inhibiting lateral expansion of the portion of the bladder residing within the fixed collar; and a slidable collar secured to the valve mechanism, the slidable collar being slidably disposed within the housing and over a range sufficient at a first extreme position to cause that portion of the bladder between the fixed collar and the slidable collar to fold upon itself, thereby providing a protected position within the housing for the valve mechanism, and sufficient at a second and opposite extreme position to fully extend that portion of the bladder between the fixed collar and the slidable collar, thereby allowing the vale mechanism to protrude axially from the housing.

* * * * *